(12) United States Patent  
Fry

(10) Patent No.: US 6,685,634 B1
(45) Date of Patent: Feb. 3, 2004

(54) PORTABLE PHYSIOLOGICAL MONITOR INCLUDING BODY-PART-ENCIRCLING GPS ANTENNA

(76) Inventor: William R. Fry, 25 Lambrig Way, Colorado Springs, CO (US) 80906

( * ) Notice: Subject to any disclaimer, the term of this patent is extended or adjusted under 35 U.S.C. 154(b) by 0 days.

(21) Appl. No.: 10/352,399

(22) Filed: Jan. 28, 2003

(51) Int. Cl.[7] .............................. A61B 5/00; A61B 5/02; A61B 5/04; H04B 7/185
(52) U.S. Cl. ...................... 600/300; 128/903; 128/905; 342/357.06; 600/481; 600/509; 600/523
(58) Field of Search ...................... 342/357.01–357.17; 128/903, 905; 600/300–595; 455/575.2

(56) References Cited

U.S. PATENT DOCUMENTS

| | | | |
|---|---|---|---|
| 4,754,285 A | 6/1988 | Robitaille | 343/718 |
| 4,981,141 A | 1/1991 | Segalowitz | 128/696 |
| 5,008,864 A | 4/1991 | Yoshitake | 368/10 |
| 5,757,332 A | 5/1998 | Hanaoka et al. | 343/787 |
| 5,771,001 A * | 6/1998 | Cobb | 342/357.07 |
| 5,790,477 A | 8/1998 | Hauke | 368/10 |
| 5,853,005 A * | 12/1998 | Scanlon | 600/459 |
| 5,884,199 A | 3/1999 | Maki | 455/575 |
| 5,960,366 A | 9/1999 | Duwaer | 455/556 |
| 6,075,500 A | 6/2000 | Kurz et al. | 343/895 |
| 6,246,362 B1 | 6/2001 | Tsubata et al. | 342/357.08 |
| 6,259,399 B1 | 7/2001 | Krasner | 342/357.06 |
| 6,324,418 B1 * | 11/2001 | Crowley et al. | 600/476 |
| 6,366,250 B1 | 4/2002 | McConnell | 343/718 |

* cited by examiner

Primary Examiner—Thomas H. Tarcza
Assistant Examiner—Fred H. Mull
(74) Attorney, Agent, or Firm—Gifford, Krass, Groh, Sprinkle, Anderson & Citkowski, PC

(57) ABSTRACT

A portable unit provides location-related data and physiological information to a person. The preferred embodiment includes a GPS receiver, a physiological sensor receiver, a computation unit to determine location-related data from the GPS receiver and a physiological condition from the physiological sensor, and a GPS antenna configured to encircle a body part of the user. As examples, a chest strap, wrist strap, or head strap may carry at least a part of the antenna. The physiological sensor may be a heart rate sensor, an electrocardiograph sensor, or other physiological sensor. The electronics associated with the data processor, GPS receiver or physiological sensor may be contained in an enclosure separate from the antenna, or such components may be built into the body-part-encircling antenna portion.

18 Claims, 3 Drawing Sheets

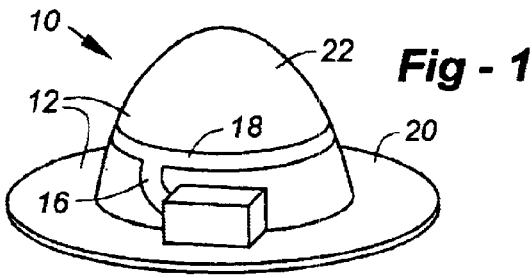
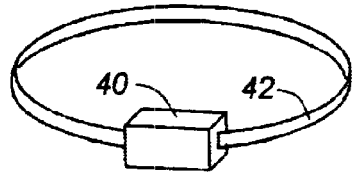
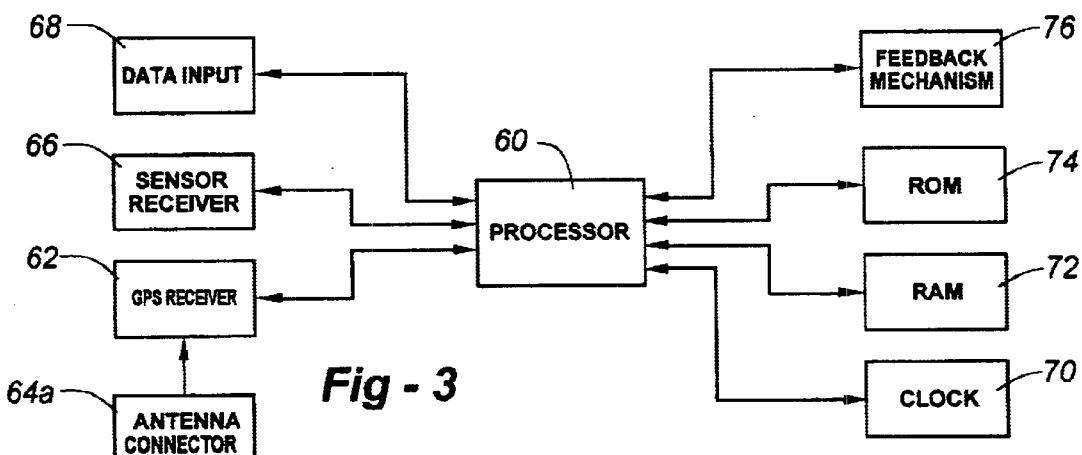
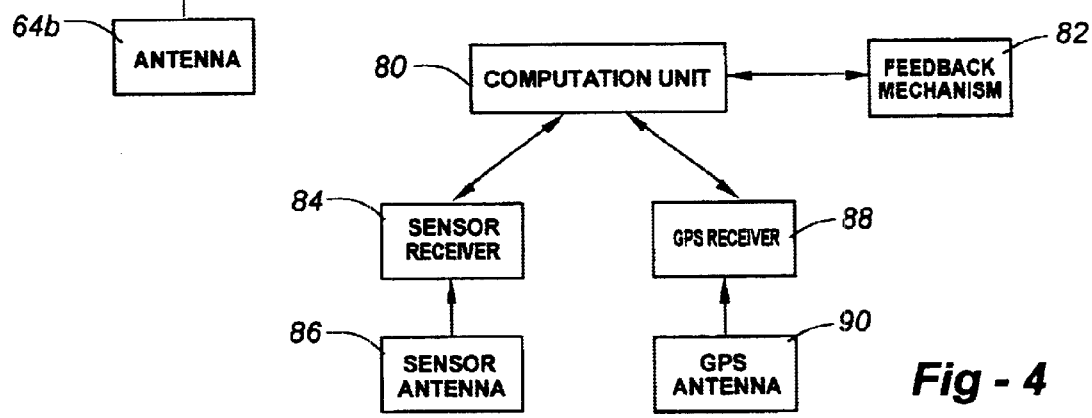

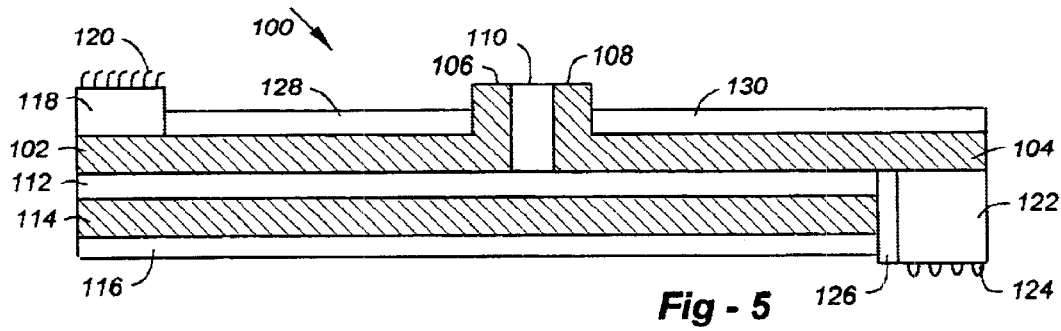
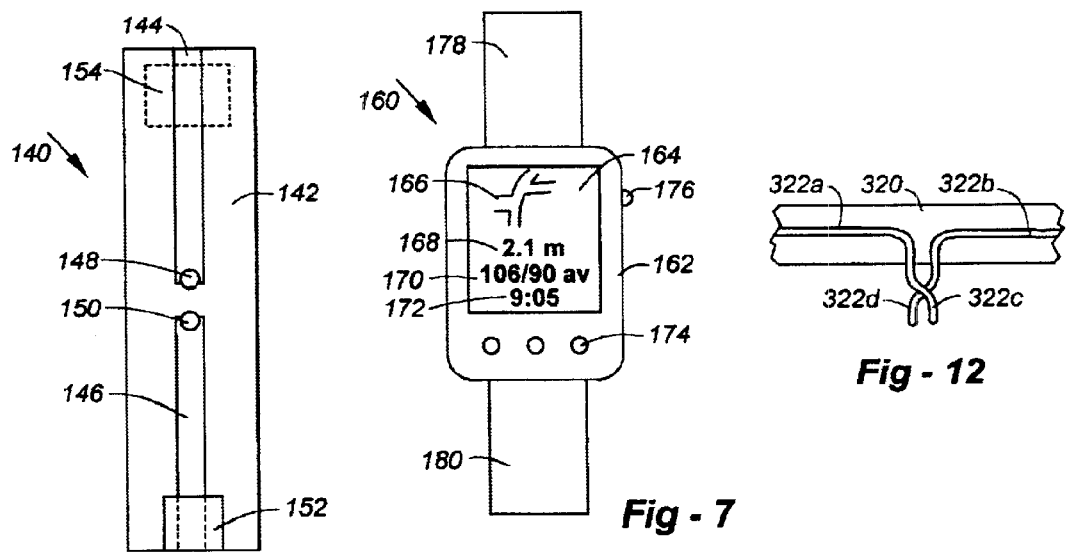
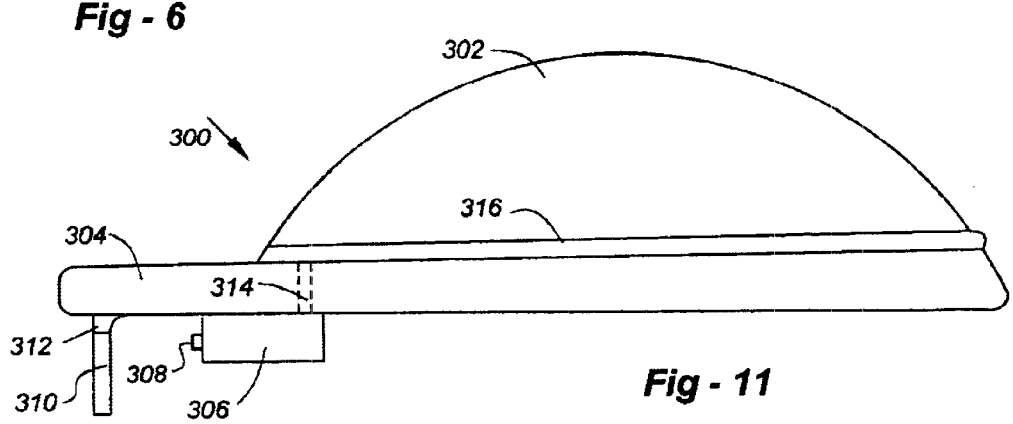

PORTABLE PHYSIOLOGICAL MONITOR INCLUDING BODY-PART-ENCIRCLING GPS ANTENNA

FIELD OF THE INVENTION

The invention relates to global positioning systems, in particular portable devices comprising a global positioning system (GPS) and one or more physiological sensors.

BACKGROUND OF THE INVENTION

Portable GPS units are known in the art. For example, U.S. Pat. No. 6,366,250, to McConnell describes a wrist-mounted wireless instrument and antenna apparatus, having a wrist strap containing an antenna and an electrical shield. Various strap antenna configurations are discussed in the background of this patent. U.S. Pat. No. 6,259,399 to Krasner discloses garments containing GPS receivers. U.S. Pat. No. 6,246,362 to Tsubata discloses a portable GPS signal receiving apparatus. U.S. Pat. No. 5,884,199 to Maki discloses a portable wireless receiver having a GPS function, where the antenna is disposed in the upper portion of the speaker/microphone unit. U.S. Pat. No. 5,790,477 to Hauke discloses a watch also comprising a GPS receiver with antenna.

Other portable wireless devices are known in the art. For example, U.S. Pat. No. 6,075,500 to Kurz et al discloses a compact antenna for a portable radio apparatus, where the antenna may have a zigzag configuration. U.S. Pat. No. 5,960,366 to Duwaer discloses a wrist-watch wireless telephone. U.S. Pat. No. 5,757,332 to Hanaoka discloses a flexible carrying strap for an electronic apparatus also functioning as a loop antenna. U.S. Pat. No. 5,008,864 to yoshitake discloses a radio telephone in the form of a wristwatch, with an antenna portion on the carrying strap. U.S. Pat. No. 4,981,141 to Segalowitz discloses a wireless electrocardiographic monitoring system. U.S. Pat. No. 4,754,285 to Robitaile discloses an expansion band antenna for a wristwatch application.

SUMMARY OF THE INVENTION

This invention resides in a portable unit for providing location-related data and physiological information to a person. The preferred embodiment includes a GPS receiver, a physiological sensor receiver, a computation unit to determine location-related data from the GPS receiver and a physiological condition from the physiological sensor, and a GPS antenna configured to encircle a body part of the user. As examples, a chest strap, wrist strap, or head strap may carry at least a part of the antenna.

The physiological sensor may be a heart rate sensor, an electrocardiograph sensor, or other physiological sensor. The electronics associated with the data processor, GPS receiver or physiological sensor may be contained in an enclosure separate from the antenna, or such components may be built into the body-part-encircling antenna portion.

BRIEF DESCRIPTION OF THE DRAWINGS

FIG. 1 shows a portable unit comprising a head-encircling antenna;

FIG. 2 shows an embodiment supported by a strap;

FIG. 3 shows a schematic of an electronic circuit;

FIG. 4 shows a schematic of a system configuration;

FIG. 5 shows a cross section of a strap comprising an antenna;

FIG. 6 shows a top view of a strap comprising an antenna;

FIG. 7 shows a wrist mounted device having a display;

FIG. 11 shows a hat having an antenna that substantially encircles the head of a person; and FIG. 12 shows an electrical connection to an antenna included within a strap.

DETAILED DESCRIPTION OF THE INVENTION

Figure 8:
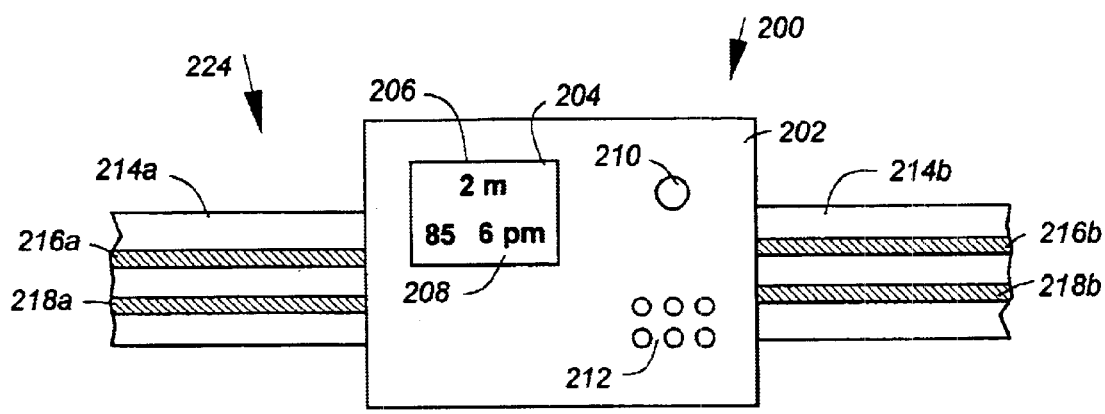
FIG. 8 shows a strap mounted device.

FIG. 1 shows a portable unit, shown generally at 10, comprising a headwear item 12, comprising brim 20 and cap 22, supporting a housing 14 which encloses an electrical circuit, which has an electrical connector 16 in electrical communication with an antenna substantially encircling the headwear item 12, the antenna being disposed within band 18.

The electrical circuit, described in more detail below, comprises a GPS receiver which is receives an antenna signal from the antenna. The band comprises an antenna which encircles the head of a person when the headwear item is supported by the head of the person. The brim or cap can be used to support housing which includes the GPS receiver.

FIG. 2 shows another embodiment of a portable unit according to the present invention. A headwear item in the form of a headband 42 encircles the head of a person. The headband supports a housing 40 which contains a GPS receiver. The GPS receiver is in electrical communication with an antenna 46 which is disposed within the headband 42. For example, a wire or other electrical conductor may be included within a fabric material.

FIG. 3 shows a schematic of an electronic circuit which can be used in embodiments of the present invention. The circuit comprises processor 60, GPS receiver 62, physiological sensor receiver 66, data input mechanism 68, clock 70, RAM 72, ROM 74, and feedback mechanism 76.

Antenna signals are received from an antenna 64b, which is in electrical communication with the GPS receiver 62 through electrical connector 64a. In some embodiments, the electrical connector between the electrical circuit and, for example, a loop of wire, may form a useful part of an antenna. Antenna signals are received by GPS receiver 64. The GPS receiver 62 passes location-related data to the processor 60.

The physiological sensor receiver receives a physiological sensor signal from a physiological sensor, which may be disposed within the same housing as includes the electrical circuit, or can otherwise be supported by the subject.

In one embodiment the physiological sensor is a heart rate sensor. The physiological signal in this embodiment will be a signal correlated with heart rate. For example, a sequences of pulses, amplitude or frequency modulation of a carrier frequency, or other signal can be correlated with heart rate. The physiological sensor receiver provides a physiological signal to the processor, for example a digital representation of heart rate, time period between heartbeats, or other signal from which the heart rate can be calculated.

The feedback mechanism may comprise a visual display, indicator lamp or lamps, bar graph, audio alert, voice synthesis unit, vibrating mechanism, or some combination of devices.

A telemetric heart rate measuring device is described in U.S. Pat. No. 6,405,077 to Birnbaum et al. As is known in the art, a heart rate sensor can be disposed on a strap encircling the torso of the subject. A heart rate sensor may comprise electrodes, in contact with the skin of the subject, at least one amplification stage, and a wireless transmission stage, which may comprise a coil, for example as disclosed in U.S. Pat. No. 6,405,077.

FIG. 4 shows a simplified schematic of an embodiment according to the present invention, comprising a computation unit 80, feedback mechanism 82, physiological sensor receiver 84, sensor antenna 86, GPS receiver 88, and GPS antenna 90.

FIG. 5 illustrates, in cross-section, a strap incorporating an antenna, which may be used in embodiments of the present invention. The strap, shown generally at 100, comprises flexible conducting strips 102 and 104, with electrical connectors 106 and 108 to an electrical circuit (not shown), so that an antenna comprises the conducting strips. A conductive hook-and-loop closure mechanism, comprising conducting regions 118 and 122, hooks 120, and loops 124, provide an electrical path between strips 102 and 104 when the hook-and-loop closure mechanism is closed. A conducting strip 114 provides electrical shielding. Flexible, electrically insulating strips 116, 112, 128, and 130 may be provided so as to mechanical strength, electrical insulation, aesthetic appeal, or other purpose. The strap components may be laminated together, or the conductive strips run through guides in one or more pieces of fabric. Insulating region 126 isolates the conducting closure mechanism part 122 from the electrical shielding strip 114. Insulating regions may be omitted, so that conductive strips are exposed if desired.

FIG. 6 shows a top view of a strap, shown generally at 140, which may have a cross-section similar to that shown in FIG. 5. The strap comprises a flexible electrical insulator 142, conducting strips 144 and 146, which may be joined electrically by an electrically conducting closure mechanism comprising elements 152 (on top of the strap) and 154 (below the strap). For example, the closure mechanism may be a hook and loop type. Electrical connectors 148 and 150 provide an electrical path to an electrical circuit. Hence, connectors 148 and 150, conductive strips 144 and 146, and the electrically conductive closure mechanism together form a loop antenna.

FIG. 7 shows an improved system according to the present invention. The system comprises a wrist-mounted device, shown generally at 160, comprising a housing 162, display 164, control buttons such as 174, control button 176, and strap comprising first strap part 178 and second strap part 180. The display shows a map 166, exercise data (distance covered) 168, heart rate data (including current and average) 170, and time 172.

The first and second strap parts (178 and 180) encircle a wrist or other body part of a person, and may have any convenient closure mechanism, such as a hook-and-loop closure or a buckle. Alternatively, the first and second strap parts may be sections of a single continuous strap. The strap comprises an antenna, for example in the form of electrical conductor within a flexible non-conducting material, a metal strap (such are used with conventional wristwatches, and the like. The antenna is used as a GPS antenna for a GPS receiver within the housing.

The display may be a liquid crystal display, light emitting display, or other visual display. The control buttons can be used to set the operating mode of the device, enter parameters, store and retrieve data, and the like.

FIG. 8 shows a strap-supported device, shown generally at 200, comprising housing 202, display 204, indicator lamp 210, and an audio alert behind grille 212. The housing 202 is supportable using a strap 224, which is adapted to encircle a body part of the person.

In this example, the strap comprises flexible insulating region 214. Parts 214a and 214b may be ends of a loop, or may have an closure mechanism such as a buckle or hook-and-loop closure mechanism. The strap also comprises two antennas, a first antenna for receiving wireless signals from a physiological monitor, and a second antenna for receiving GPS signals. In this example, the GPS antenna comprises conductors 218a and 218b, which are in electrical communication so as to substantially encircle the body parts of the person when the strap 224 supports the device 200. The second antenna comprises conductors 216a and 216b, which may or may not encircle the body part, providing a dipole or loop antenna as desired.

Figure 9:
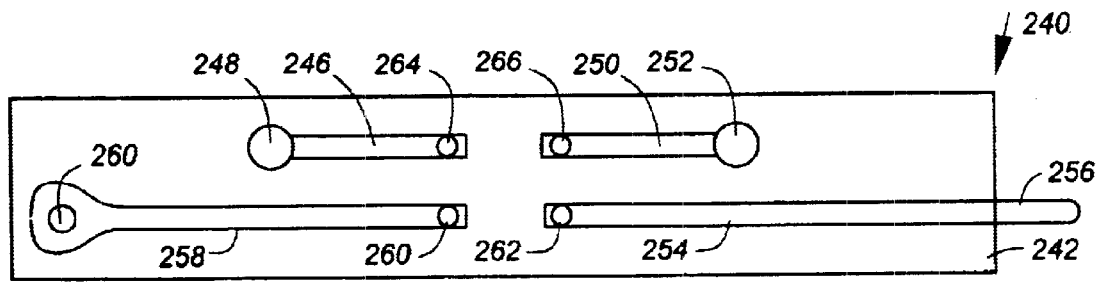
FIG. 9 shows a view of a strap comprising an antenna.

FIG. 9 shows a strap, shown generally at 240, comprising a flexible insulating material 242, electrical conductors 246, 248, 250, and 252 (which together form a first antenna), and electrical conductors 258 and 254 (which together form a second antenna). Electrical connectors 260, 262, 264, and 266 provide electrical connections to electrical circuitry contained within a housing supported by the strap (not shown for convenience).

The strap 240 may encircle a body parts of the person, and the tongue 256 placed through the hole 260 to help secure the strap. Other buckle parts may be used, which are not shown for convenience. When the strap encircles the body part of the person, the second antenna comprises an electrically conducting path which substantially encircles a body parts so as to form a loop antenna. The first antenna comprises an electrically conducting path which does not substantially encircle the body part, so as to form a dipole antenna. The loop antenna may be used as a GPS antenna, and the dipole antenna used to receive wireless signals from a physiological monitor mounted elsewhere on the person's body.

An insulating, protective, or shielding layer may be used to cover exposed electrical conductors.

Electrical conductive regions 248 and 252 may be omitted in the example above. In another embodiment, electrical conductors 248 and 252 are proximate to the skin of a person, so as to receive an electrical signal from the body of the person. This electrical signal may correlate with heart rate, or may be used to determine an EKG for the person.

Figure 10:
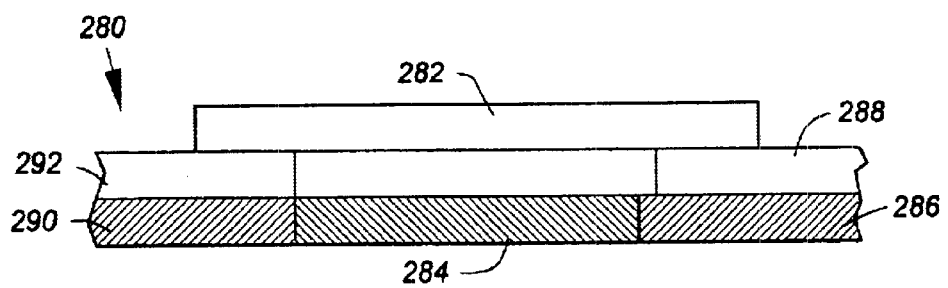
FIG. 10 shows a strap comprising an antenna having a flexible section.

FIG. 10 shows a cross-section of part of a band 280 comprising flexible regions 292 and 288 interconnected by elastomeric strip 282. Flexible electrical conductors 290 and 286 are in electrical communication using braided conductive material 284. For example, the elastomeric strip may be conventional fabric elastic, and the braided conductive material may be braided copper, such as used on coaxial cables.

FIG. 11 shows another embodiment adapted to be worn on the head of the person, the portable unit shown generally at 300, comprising hat 302 having brim 304, and a band 316 encircling the hat so as to substantially encircle the head of the person when the hats is supported by the head of the person. An electrical connector 314 links an electrically conductive path within the band 316 to an electrical circuit contained within housing 306. The housing 306 contains an electric circuit adapted to determine location related information from a GPS signal received using an antenna, the antenna comprising the electrical connector 314 and the conductive path included within band 316 which substantially encircles the head of the person when the person wears the hat.

Location related data, such as position, altitude, speed, longitude, latitude and the like may be displayed on screen 310, which is supported by hinges 312 from the brim 304 of the hat. Information may be projected so as to be viewable by the person using projection unit 308, supported by the housing 306, which may provide a scanned laser beam.

FIG. 12 shows in more detail how an electrical connector is in electrical communication with a conductive path within a band comprising an antenna. Flexible material 320 forms of band which may encircle a body parts of the person. The band comprises electrical conductor 322, shown as two ends of a loop at 322a and 322b. The loop hence substantially encircles the body part of the person when the band is placed around the body part. The conductor may be brought out of the band at 322c and 322d so as to provide an electrical connector to an electrical circuit, so as to provide antenna signals to the electrical circuit.

In other embodiments, a GPS antenna may comprise multiple turns of an electrical conductor, such as a wire, around a body part of a person. Two, three, four, five, six, or more turns of a conductor around the body part may be provided, so as to provide a multiple-turn loop antenna.

Conductive materials include metals (such as copper, aluminum, silver, gold, other metals and alloys), conductive polymers, conducting composites, carbon-based materials, semiconductors, and other conductive substances as known in the arts. Antennas may comprise wires (single wires, braided wires, cables, coated wires, and the like), strips, tubes, coatings (for example, metal coated plastics), flexible sheets, laminated materials, multilayers, chains, segmented structures (such as steel watchstraps), conducting fabrics, conductor-infused materials (such as graphite-infused fabrics) and the like.

Insulating materials, for use in straps, include plastics, plant-derived materials, and the likes. Insulators may take the form of include fabrics, flexible sheets, and the like.

In some embodiments, a band may be formed of a conducting material. An insulating region may be disposed at some position, so as provide a break within an otherwise conducting loop, with electrical connectors leading from each side of the insulating region to a GPS receiver.

An antenna may be disposed around the collar of an item of clothing, with electrical connectors leading from the antenna to a GPS receiver, for example supported within a pocket of the item of clothing. Electrical connectors may be removable so as to assist cleaning.

An antenna may be disposed within a headband, wristband, chest-strap, belt, and the like. For example, a chest-mounted heart rate monitor may also comprise a GPS receiver having an antenna included within at least part of the supporting chest band.

Embodiments described are not intended to be limiting. Configurations and elements from described examples may be combined in ways other than those specifically described. Other embodiments will be clear to those skilled in the arts Having described my invention, I claim:

1. A portable unit for providing location-related data and physiological information to a person, comprising:
   a housing;
   a GPS receiver, contained within the housing;
   a physiological sensor receiver, contained within the housing and operable to receive a sensor signal from a physiological sensor;
   a computation unit, contained within the housing, wherein the computation unit is adapted to determine location-related data from GPS data provided by the GPS receiver, and to determine a physiological condition from physiological data provided by the physiological sensor; and
   an antenna, in electrical communication with the GPS receiver, adapted to encircle a body part of the person.

2. The portable unit of claim 1, further comprising a strap adapted to encircle the body part of the person, so as to allow the housing to be supported by the body part of the person, wherein the strap comprises at least part of the antenna.

3. The portable unit of claim 1, wherein the physiological sensor is a heart rate sensor.

4. The portable unit of claim 1, wherein the physiological sensor is supported by the housing.

5. The portable unit of claim 1, wherein the physiological sensor is supported by the body of the person.

6. The portable unit of claim 1, wherein the physiological sensor is an electrocardiograph sensor.

7. The portable unit of claim 1, wherein the antenna is also in electrical communication with the physiological sensor receiver.

8. The portable unit of claim 1, wherein the computation unit is further adapted to show the location-related data and physiological condition on a display supported by the housing.

9. The portable unit of claim 1, wherein the body part is a wrist of the person.

10. The portable unit of claim 1, wherein the body part is a torso of the person.

11. The portable unit of claim 1, wherein the body part is a head of the person.

12. A portable unit for providing location information to a person, comprising:
    a headwear item, adapted to be supported on a head of the person;
    a GPS receiver, supported by the headwear item;
    an antenna, in electrical communication with the GPS receiver, substantially encircling the headwear item so that the antenna substantially encircles the head of the person when the headwear item is supported by the head of the person;
    a computation unit, receiving GPS data provided by the GPS receiver, adapted to determine location-related data to the person.

13. The portable unit of claim 12, further comprising a feedback mechanism, wherein the computation unit is further adapted to provide location-related data to the person through the feedback mechanism.

14. The portable unit of claim 13, wherein the feedback mechanism comprises an audio device, supported by the headwear item so as to be audible to the person when the audio device is energized.

15. The portable unit of claim 13, wherein the feedback mechanism comprises a visual display, supported by the headwear item so as to be viewable by the person when the headwear item is supported by the head of the person.

16. The portable unit of claim 12, further comprising a physiological sensor receiver, adapted to receive a physiological signal from a physiological sensor proximate to the body of the person, and wherein the computation unit is further adapted to determine a physiological condition of the person from the physiological data provided by the physiological sensor receiver, and to provide the physiological condition to the person using the feedback mechanism.

17. The portable unit of claim 16, wherein the physiological condition is a current heart rate of the person.

18. The portable unit of claim 16, wherein the physiological condition comprises a cardio-vascular parameter.

* * * * *